(12) United States Patent
Metz et al.

(10) Patent No.: US 6,929,917 B2
(45) Date of Patent: Aug. 16, 2005

(54) METHOD FOR CLONING OF A RARE, SPECIFICALLY MUTATED CELL

(75) Inventors: Richard Metz, Lawrenceville, NJ (US); Mike DiCola, Flemington, NJ (US); R. Michael Blaese, New Hope, PA (US)

(73) Assignee: PreGentis, New Town, PA (US)

( * ) Notice: Subject to any disclaimer, the term of this patent is extended or adjusted under 35 U.S.C. 154(b) by 0 days.

(21) Appl. No.: 10/298,850

(22) Filed: Nov. 18, 2002

(65) Prior Publication Data

US 2004/0096832 A1 May 20, 2004

(51) Int. Cl.$^7$ .................. C12N 15/09; C12N 15/00; C12N 21/00; C12N 15/85; C12Q 1/68
(52) U.S. Cl. .................. 435/6; 435/468; 435/471; 435/69.1; 435/69.7; 435/70.1; 435/71.1; 435/440; 435/325; 435/252.1; 435/254.2
(58) Field of Search .................. 435/455, 471, 435/6, 69.1, 69.7, 71.1

(56) References Cited

U.S. PATENT DOCUMENTS

| | | | |
|---|---|---|---|
| 6,010,908 | A | 1/2000 | Gruenert et al. |
| 6,210,891 | B1 | 4/2001 | Nyren et al. |
| 6,271,360 | B1 | 8/2001 | Metz et al. |
| 2002/0119570 | A1 * | 8/2002 | Yoon et al. ............ 435/455 |

FOREIGN PATENT DOCUMENTS

| | | |
|---|---|---|
| WO | WO 98/54330 | 12/1998 |
| WO | WO 99/07865 | 2/1999 |
| WO | WO 01/15740 | 3/2001 |

OTHER PUBLICATIONS

Bartlett et al. Nat. Biotech., 2000; 18:615–22.*
Bartlett and Winand et al. AJVR, 1996; 57(5):650–4.*
Yoon et al. PNAS, 1996 ; 93 :2071–76.*
Alexeev et al. Nat. Biotech. 2000 ; 18 :43–7.*
Metz et al. Chest, 2002; 121(3):91s–97s.*
Cole–Strauss et al. Nuc. Acids Res. 1999; 27(5):1323–30.*
Faruqi et al., "Peptide nucleic acid–targeted mutagenesis of a chromosomal gene in mouse cells", Proc. Natl. Acad. Sci. USA, vol. 95, pp. 1398–1403, Feb. 1998.
Havre et al., "Targeted mutagenesis of DNA using triple helix–forming oligonculeotides linked to psoralen", Proc. Natl. Acad. Sci. USA, vol. 90, pp. 7879–7883, Aug. 1993.
Raha et al., "Mutagenesis by third–strand–directed psoralen adducts in repair–deficient human cells: High frequency and altered spectrum in a xeroderma pigmentosum variant", Proc. Natl. Acad. Sci USA, vol. 93, pp. 2941–4946, Apr. 1996.
Faruqi et al., "Triple–Helix Formation Induces Recombination in Mammalian Cells via a Nucleotide Excision Repair–Dependent Pathway", Molecular and Cellular Biology, Feb. 2000, pp. 990–1000.

(Continued)

Primary Examiner—Gerry Leffers
Assistant Examiner—Ramin Akhavan
(74) Attorney, Agent, or Firm—Fish & Neave IP Group

(57) ABSTRACT

The invention concerns a new method of detecting a rare product of a directed genetic alteration of a cultured cell. The method is applicable to any method of making the alteration provided that a pair of closely linked alterations can be made. The method consists of sequentially using allele specific polymerase chain reaction (PCR) to preferentially amplify sequences containing one of the two linked alterations coupled with a second method that detects the second change in the PCR product. The second method can be restriction digestion, traditional sequencing or pyrosequencing. Experiments indicate that alterations as rare as one correctly altered copy in 10,000 cells can be detected.

27 Claims, 1 Drawing Sheet

OTHER PUBLICATIONS

Michael Seidman and Peter Glazer, "The potential for gene repair via triple helix formation", The Journal of Clinical Investigation, Aug. 2003, vol. 112, No. 4, pp. 487–494.

Barre et al., "Unambiguous demonstration of triple–helix–directed gene modification", PNAS, Mar. 28, 2000, vol. 97, No. 7, pp. 3084–3088.

Cole–Strauss, et al., "Correction of the Mutation Responsible for Sickle Cell Anemia by an RNA–DNA Oligonucleotide", 1996, Science 273, 1386–89.

Gamper et al., "The DNA strand of chimeric RNA/DNA oligonucleotides can direct gene repair/conversion activity in mammalian and plant cell–free extracts", 2000, NAR 28, 4332–39.

Goncz et al., "Targeted replacement of normal and mutant CFTR sequences in human airway epithelial cells using DNA fragments", 1998, Hum. Mol. Genetics 7, 1913.

Kunzelmann et al., "Gene targeting of CFTR DNA in CF epithelial cells", 1996, Gene Ther. 3, 859.

Beetham et al., "A tool for functional plant genomics: Chimeric RNA/DNA oligonucleotides causes in vivo gene–specific mutations", 1999, Proc. Natl. Acad. Sci. 96, 8774.

Zhu et al., "Targeted manipulation of maize genes in vivo using chimeric RNA/DNA oligonucleotides", 1999, Proc. Natl. Acad. Sci. 96, 8768.

Parekh–Olmedo, H., et al., "Targeted Nucleotide Exchange in *Saccharomyces cerevisiae* Directed by Short Oligonucleotides Containing Locked Nucleic Acids", 2002, Chem. Biol. 9, 1073–84.

Liu, L., et al., "Rad51p and Rad54p, but not Rad52p, elevate gene repair in *Saccharomyces cerevisiae* directed by modified single–stranged oligonucleotide vectors", 2002, NAR 30, 2742–50.

Liu, L., et al., "Strand Bias in Targeted Gene Repair is Influenced by Transcriptional Activity", 2002, Mol. Cell. Biol. 22, 3852–63.

Bottema, C.D., & Sommer, S.S., 1993, "PCR amplification of specific alleles: Rapid detection of known mutations and polymorphisms", Mutation Research 288, 93–102.

Kirby, G.M., et al., "Allele–Specific PCR Analysis of P53 Codon 249 Agt Transversion in Liver Tissues From Patients With Viral Hepatitis", 1996, Int. J. Cancer 68, 21–25.

Ronaghi et al., "A Sequencing Method Based on Real–Time Pyrophosphate", 1998, Science 281, 363.

Ronaghi et al., "Improved Performance of Pyrosequencing Using Single–Stranded DNA–Binding Protein", 2000, Anal. Biochem. 286, 282–8.

Hochberg, E.P. et al., "A novel rapid single nucleotide polymorphism (SNP)–based method for assessment of hematopoietic chimerism after allogeneic stem cell transplantation", 2002, Blood, 101(1):363–9.

Oliver et al., "Use of Single Nucleotide Polymorphism (SNP) and Real–Time Polymerase Chain Reaction for Bone Marrow Engraftment Analysis", 2000, Journal of Molecular Diagnostics. 2(4), 202–208.

Shitaye et al., "A Novel Method for Assigning TAP1 Genotype Using Restriction Enzyme Plus PASA Methodology", 1999, Hum Immunol. 60(12), 1289–92.

Sarkar et al., "Restriction–site PCR: A Direct Method of Unknown Sequence Retrieval Adjacent to a Known Locus by Using Universal Primers", 1993, PCR Methods Appl 2(4): 318–322.

\* cited by examiner

METHOD FOR CLONING OF A RARE, SPECIFICALLY MUTATED CELL

FIELD OF THE INVENTION

The invention concerns the process making a specific directed change in the genome of a cultured cell. More specifically, the invention concerns a process for detecting and isolating a cell having the specific desired change from a culture in which such cells are rare. The sequence-specific process for making genetic change is also called gene editing or directed mutation

BACKGROUND OF THE INVENTION

A variety of sequence-specific processes have been developed that make a specific, directed genetic alteration in a cultured cell. The desired alteration most often is a nucleotide mutation, for example to correct a genetic defect or to introduce an in-frame stop codon and thereby "knock-out" the target gene. The methods have in common the step of introducing into the cells of the culture an exogenous nucleic acid having the desired sequence, i.e., the exogenous nucleic acid "encodes" the desired mutation. The exogenous nucleic acid can be a duplex "hairpin" "chimeric" oligonucleotide of between about 40 and 100 nucleotides including 2' alkoxy substituted ribonucleotides (Cole-Strauss, et al., 1996, Science 273, 1386–89), an end-protected olignucleotide (WO 01/15740; Gamper et al., 2000, NAR 28, 4332–39) or unprotected DNA fragments of between about 100 and 2000 nucleotides, which can be optionally separated so that the introduced nucleic acid is substantially free of either the sense or antisense strand. Goncz et al., 1998, Hum. Mol. Genetics 7, 1913; Kunzelmann et al., 1996, Gene Ther. 3, 859; U.S. Pat. No. 6,010,908. The exogenous nucleic forms a duplex with the homologous region of the genomic DNA (the "target genomic fragment") and the cell's enzymatic machinery causes the desired mutation in the target genomic fragment.

Chimeric hairpin oligonucleotides can be used to mutate plant cells. Beetham et al., 1999, Proc. Natl. Acad. Sci. 96, 8774; Zhu et al., 1999, Proc. Natl. Acad. Sci. 96, 8768; WO 98/54330; WO 99/07865; WO 99/07865.

A sequence-specific process to induce mutations in yeast using phosphorothioate end-protected single stranded oligonucleotides has been developed and 2'O-4' methylene bl;ocked oligonucleotides. Parekh-Olmedo, H., et al., 2002, Chem. Biol. 9, 1073–84; Liu, L., et al., 2002, NAR 30, 2742–50; Liu, L., et al., 2002, Mol. Cell. Biol. 22, 3852–63.

A problem that has limited the use of sequence-specific processes is that the fraction of the cultured cells that contain the desired mutation can be very small. Under these circumstances there is no practical way to identify and clone the altered cells unless the desired alteration confers some selectable phenotype, such as drug resistance, or a grossly visible phenotype that permits cloning by inspection.

Techniques have been developed to permit the detection of single nucleotide mutation in cultured cells. One common technique is allele specific polymerase chain reaction (AS-PCR). PCR is the technique whereby two primers are used to amplify a template sequence using bacterial enzymes in a cell free system. The DNA polymerase employed in PCR requires that the primer be hybridized (Watson-Crick paired) to the template DNA for synthesis to occur. Therefore, if the hybridization conditions are made sufficiently stringent, a single nucleotide mismatch between template and one of the two primers can cause a readily detectable difference in the amount of DNA that is synthesized in the PCR process. This technique permits the use of allele specific primers to distinguish the genotype of a homogeneous DNA sample from an allelic genotype that differs by a single nucleotide mutation. Particular attention has been drawn to the effects of mismatches at the 3' end of the primer. Reviewed, Bottema, C. D., & Sommer, S. S., 1993, Mutation Research 288, 93–102.

However, AS-PCR is a reportedly satisfactory method to detect a rare cell of one genotype in the presence of the allelic genotype only up to a sensitivity of 1 in 100. Kirby, G. M., et al., 1996, Int. J. Cancer 68, 21–25. Experience has shown that when the hybridization stringency is high enough to suppress amplification of the unwanted allele, i.e., to prevent false positives, AS-PCR becomes insensitive to the presence of the rare cell having the correct allele.

In addition to AS-PCR, other techniques have been developed to readily detect single nucleotide differences in small samples of DNA. The oldest is the restriction enzyme technology that is used to detect restriction fragment length polymorphism (RFLP). Restriction enzymes are DNA endonucleases that cut the DNA polymer whenever they encounter a specific nucleotide sequence that is typically a palindrome between 4 and 8 nucleotides in length. Other techniques include direct sequencing, in particular, the technique called "pyrosequencing" uses a luciferase-based detection of the production of pyrophosphate (a phosphoric acid anhydride), which occurs during DNA polymerization. Ronaghi et al., 1998, Science 281, 363; Ronaghi et al. 2000, Anal. Biochem. 286, 282–8; U.S. Pat. No. 6,210,891. Pyrosequencing has been shown to be effective in detecting a single nucleotide difference in as few as one in 20 cells, but not fewer. Hochberg, E. P., et al., 2002, entitled: "A novel rapid single nucleotide polymorphism based method for assessment of hematopoietic chimerism" Blood [e-published at www.bloodjouurnal.org].

There remains a need for a method of detecting mutant cells at frequencies less than one in 20.

SUMMARY OF THE INVENTION

The invention is a new and improved method for reliably detecting the presence of a rare cell having a desired nucleotide mutation that was introduced by a sequence-specific process. According to the invention AS-PCR is conducted at a reduced level of hybridization stringency, such that the amount of product is not significantly affected by the presence or absence of the desired mutation. Unexpectedly, when AS-PCR is so conducted and the desired mutation is present at the level as low as 1 part in 10,000, the AS-PCR product will contain the desired mutation at a level greater than one part in about 20.

This discovery permits the detection with great sensitivity and specificity of two closely linked nucleotide mutations. A first mutation is used in a reduced stringency AS-PCR to selectively amplify a target fragment that contains both mutations. The amplified second mutation can be readily detected in the AS-PCR product by RFLP or direct sequencing.

The invention, therefore, consists of designing an exogenous nucleic acid for a sequence-specific process to contain a desired mutation and a closely linked companion mutation. In one embodiment the desired mutation is detected by AS-PCR and the companion mutation introduces a novel restriction site that is detected by RFLP. The mutations are separated by a convenient distance that is dependent on the sequence-specific process, which is typically from 1 to 50 nucleotides. A culture is treated with the exogenous nucleic acid and replicate subcultures made. Genomic DNA is made from one replicate for testing and a second replicate is reserved. The further subdivisions are made from the reserved replicate of the positive subculture until clones having the desired mutation are obtained. The subdivided positive subcultures can be tested using the method of the invention or, when practical, RFLP.

DETAILED DESCRIPTION OF THE INVENTION

Figure 1:
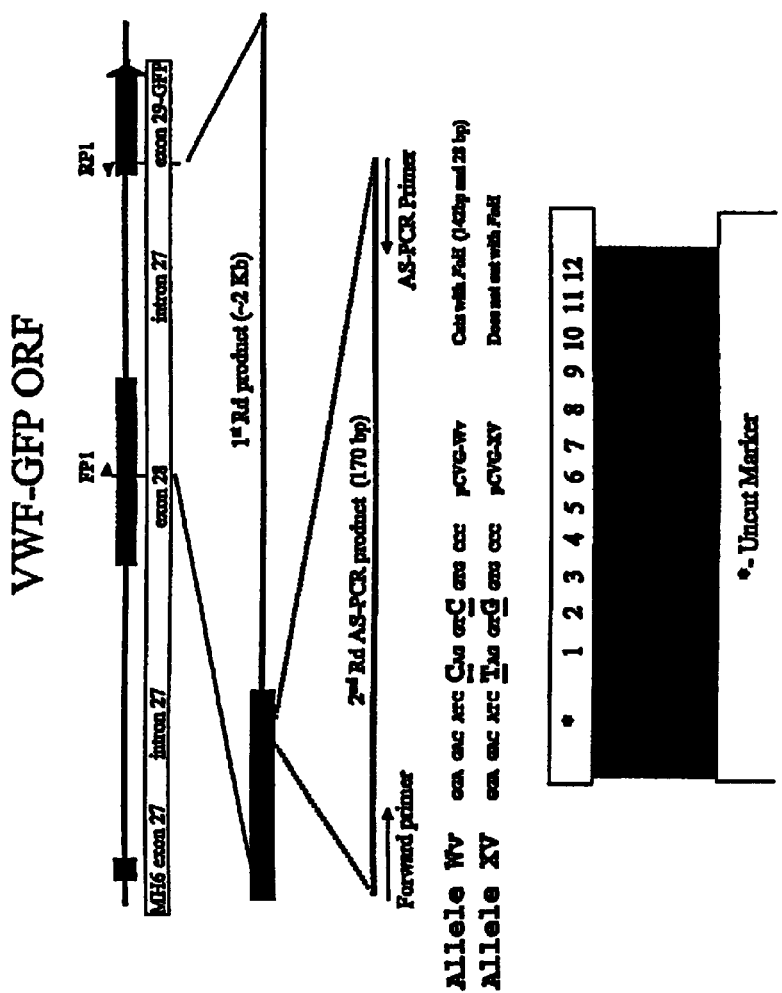
FIG. 1 shows the embodiment of the invention that distinguishes two alleles (SEQ ID NOS: 7–8) of Factor VIII Binding Protein (von Willebrand's Factor).

The implementation of the detection method of the invention is substantially unaffected by the choice of the sequence-specific process that is used to introduce the mutation. The culture is treated with the exogenous nucleic acid that encodes the desired mutation and the companion mutation in the target genomic fragment and subcultures made. The desired mutation and the companion mutation can be adjacent nucleotide mutations or may be separated by a convenient distance. The more widely separated the mutations are the more easily the RFLP analysis can be performed. However, too wide separation would result in the loss of linkage between the mutations in the sequence-specific process. When SFHR is used as a sequence-specific process, a separation of up to about 50 nucleotides is convenient.

The method of the invention requires two PCR processes, the product of the first being used as the template of the second. The first PCR is a conventional PCR and the second is an AS-PCR.

For convenience we introduce the following nomenclature related to PCR. The template DNA is an antiparallel duplex and consists of complementary sense and antisense strands. PCR employs a template duplex and two primers one complementary to the sense strand and one that is complementary to the antisense strand. In PCR, all DNA polymerization occurs by addition of 5' dNTP to the 3' end of the primer and release of pyrophosphate. DNA is conventionally represented with the 5' end on the left and the 3'. Accordingly, the primer that is complementary to and binds the antisense strand is the "forward" primer (polymerization moving left to right) and the primer that is complementary to and binds the sense strand is the "reverse" primer. However, at all stages of the reaction the sense and antisense strands are present as templates in equal amounts. Accordingly, in the reaction there is no distinction between the forward and the reverse primer.

The primers are designed using a computer program to calculate the melting temperature and to exclude self-complementarity. Suitable software is available at "www.oligos.net" from Molecular Biology Insights, Inc., Cascade CO. The melting temperature should be between 50° C. and 60° C. Primer length is between about 16 and 21 nucleotides, the length being adjusted to compensate for GC content and achieve a melting temperature in the target range.

The annealing temperature of the AS-PCR reaction must be empirically selected for each primer set using templates that are mixtures of known amounts of the mutated and nonmutated template. Good results can be obtained by initially using a 1:1 mixture running a coarse series of reaction at various temperatures and finding the lowest temperature that gives essentially no amplification from the non-mutant template. Using that temperature as a starting point a second, and finer sequence of temperatures is tested using a titration of mixtures (1:100, 1:1000 and 1:10,000) until a temperature with suitable sensitivity is determined. Typically a temperature that results in about 500–1000 fold preferential amplification can be found, i.e., a product ratio of 1:10 can be obtained from a template ratio of 1:10,000.

The first PCR process merely amplifies the target genomic fragment and eliminates the possibility of contamination of the assay with the exogenous nucleic acid. It is essential that the primers for the first PCR reaction be chosen to make impossible amplification of the exogenous nucleic acid. The genomic DNA from about 10,000 mammalian cells is the largest amount of genomic DNA that can be conveniently used in a PCR reaction. The detection of the desired mutation in one cell per 10,000 is readily achieved. The initial subcultures optimally contain about 10,000 individuals from the treated culture.

The first PCR product is diluted and used as the template of the AS-PCR process performed at reduced stringency. The primers for this reaction are termed conventionally the forward primer and the AS-PCR primer. In this reaction either primer can be complementary to either strand. The AS-PCR primer can be selected to encode either the desired or the companion mutation. Whichever mutation is encoded by the AS-PCR primer, it is preferred that that the mutation is encoded near the 3' terminal of the primer and more preferably by the 3' terminal nucleotide of the AS-PCR primer. For that reason, the mutation encoded by the AS-PCR primer is herein termed the "the 3' mutation." As the companion mutation can more readily be used to generate a restriction site, the AS-PCR primer most often encodes the desired mutation when RFLP is the secondary detection. In such case, the desired mutation would be the "3' mutation" and the companion mutation would be the "5' mutation." The forward primer is designed so that the target genomic fragment is amplified but it cannot itself encode the second mutation. Note that the terms 3' mutation and 5' mutation do not connote positions for the mutations.

It will be readily appreciated that the detection of the 3' mutation by AS-PCR preferably involves a mismatch at the 3' terminal of the AS-PCR primer. Accordingly, there is no material difference whether the 3' mutation is a substitution, deletion or insertion. Similarly, the 5' mutation can be a substitution, deletion or insertion.

The size of the first and second products is not critical to the invention. The product of the first PCR may conveniently be between about 500 and 2000 bp. The product of the AS-PCR is selected to permit ready detection of the 5' mutation. In general the second PCR product is conveniently between about 100 and 500 bp.

An alternative system to detect the 5' mutation is commercially available (PE Biosystems) under the tradename TaqMan™. The system relies upon an oligonucleotide probe labeled at opposite ends with a fluorescent dye and a quenching dye. The probe is hybridized to the AS-PCR product in the presence of Taq polymerase. Selection of suitably stringent hybridization conditions permits hybridization to the sequence containing the 5' mutation but not to the unmodified sequence. Hybridization is detected because of the 5' exonuclease activity of the polymerase, which releases the fluorescent dye from proximity to the quencher. The release results in a detectable fluorescent signal. Livak, K. J., 1999 Genetic Anal. 14, 143–149.

EXAMPLES

Example 1

In order to detect potentially rare events that do not result in a phenotype, we developed a highly sensitive screening procedure that takes advantage of SFHR's ability to alter more than one nucleotide. We reasoned that rare events (≦0.01%) would require a pooling strategy whereby transfected cells would be plated in 96 well plates at cell densities ranging from 100 to 1,000 cells per well. The plated cells would then be maintained for several doublings and split half going for analysis and half maintained for clonal isolation and further analysis. Such a pooling strategy would limit our ability to use standard molecular analysis, like sequencing or restriction fragment length polymorphism (RFLP) analyses, to detect the rare edited events in pooled populations. Moreover, since the sampling size in a standard PCR reaction is limited, ranging from $1-3\times10^4$ genome equivalents (60–180 ng of DNA in a lysate), the assay must be sensitive and specific enough to detect 10 edited alleles in the background of a sample containing at least $10^4$ cells. Allele specific PCR (AS-PCR) has been used successfully by a number of labs to detect certain polymorphisms in mixed cell populations but requires optimization, and carefully designed and purified primers. However, even carefully designed and optimized AS-PCR assays can lead to false positives, due to varying conditions brought about by cell lysis, or false negatives, because the assay is too stringent for detecting low levels (0.1%) of a particular single nucleotide polymorphism. False negatives are a great concern.

Our gene-editing strategy makes two changes in a target sequence- one that affects the function of the gene in the desired way, such as repairing the 1514 stop codon of pCmutVG, and the other introduces a closely position nucleotide change that can be functionally silent, i.e. changing GTG to GTC for pCVG-V1515v. By making two base changes it is possible to design an assay that allows for the selective amplification of a gene-edited target using AS-PCR amplification that is selective for one of the nucleotide changes followed by a secondary assay that is specific for the second nucleotide change.

Using this strategy we detected as few as 4 copies of the pCVG-V1515v template, carrying two nucleotides differences, from a sample containing 40,000 copies of the pCmutVG. We mixed two cell lines, containing either an integrated pCmutVG or pCVG1515v plasmids, at varying ratios. PCVG-V1515v expresses a functional VWF-GFP fusion differing from pCmutVG at two nucleotides-CAG at codon 1514 and a silent nucleotide change (GTG to GTC) in the adjacent codon, 1515. The pCVG-V1515v has a Fok I restriction site overlapping the wildtype 1514 codon, which is not present at the corresponding position in the mutant pCmutVG. In order to increase our sensitivity and selectivity we performed two rounds of PCR amplification. The first reaction used a primer set flanking of the SFHR targeted region. The products from the first round reaction were diluted 10,000 fold and used as a template for a second round AS-PCR reaction, which uses the AS-primer (1515AS) as a handle to selectively enrich sequences containing the V1515v sequence. The AS-PCR product (170 bp) was then digested with FokI. Uncut AS-PCR products are those that do not contain the second nucleotide change and contains the stop codon. If the AS-PCR reaction selectively enriches for the V1515v site and the second nucleotide change (CAG at position 1514) is present, Fok I will digest the AS-PCR product into a 142 and 38 bp fragments. Agarose gel electrophoresis of the digest demonstrated the selective amplification of the pCVG-V1515v template in the background of the pCmutVG template. These data show that we can detect as few as four copies of pCVG-V1515v in the background of 40,000 cells containing pCmutVG.

HEK-pCmutVG cells were transfected with SDF-V1515v SFHR molecule (defined by primer set 4740C/8350NC). Grown for two days and split into a 96 well plate at a cell density of 1000 cells per well. Following 1 week (7 doublings) the cells were split into a replicate 96 well and grown for an additional day. One plate was lysed in 50 uL of lysis buffer (50mM KCl, 10 mM Tris pH8.3, 1.0 mM $MgCl_2$ 0.1 mg/mL Gelatin, 0.45% v/v Igepal CA-630, 0.45% v/v Tween 20, and Proteinase K at 1 ug/ml) at 55° C. for 5 hours. The Proteinase K was inactivated by heating a 95° C. for 15 minutes. 10 uL of each lysate was used in the first round PCR reaction using primers 213NC/7716C and 1×PCR buffer with 1.5 mM $MgCl_2$.

The cycling conditions were as follows: 95° C. for 2 min; 35 cycles of (95° C. 45 sec, 55° C. 45 sec, and 72° C. for 1.5 min, followed by a 5 minute extension at 72° C. The first round products were then diluted in water at 1:10,000 . 10 ul of this dilution was used in the second AS-PCR reaction using primers AS-PCR NC/4740C primer set and 1×PCR buffer with 1.5 mM $mgCL_2$. The cycling conditions were as follows: 95° C. for 2 min; 35 cycles of (95° C. 30 sec, 62° C. 30 sec, and 72° C. for 30sec, followed by a 2 minute extension 72° C. 10 uL of each product was digested with 5 Units of FoK I and analyzed on a 4% agarose gel. One can also use the primers AS-PCRC and 8350NC primers coupled with DrdI.

```
First Round PCR Primers
213NC
5' TCGGGGTAGCGGCTGAAGCAC 3'          (SEQ ID NO: 1)

7716C
5' CATGGCACAAGTCACTGTGG 3'           (SEQ ID NO: 2)

AS-PCR Primers
b-8350NC
5' CCACCTGCACACAAGGTGCC 3'           (SEQ ID NO: 3)

b-4740-4720C
5' AACAGGACCAACACTGGGCTG 3'          (SEQ ID NO: 4)

AS-PCR-C
5' GGCTGCCTGGAGACATCC 3'             (SEQ ID NO: 5)

AS-PCR-NC
5' GCCCACTCCAATGGGCACG 3'            (SEQ ID NO: 6)
```

Example 2

Example 2 concerns the detection of mutations in a murine erythropoietin receptor. A stop codon was introduced into at Glu398 and a silent mutation (GCT-<GCC) was introduced at the codon encoding Ala399. The mutation convert the receptor to one that is constitutively active, conferring hormone independent growth.

A primary PCR product of about 920 bp was formed followed by an AS-PCR product of 391 bp. Detection of the conversion event was performed by the detecting the removal of a HindIII site from the wild type sequence.

First Round PCR: 50 uL reaction mixes will contain template DNA (2 ng), 30 pMoles of each primer 30 u/9511) flanking the target sequence, 0.2 mM of each dNTPs, 1.5 mM MgCl and 3 units of Taq Polymerase. Cycling conditions, 2 minute (min) denaturation at 95° C.; followed by 35 cycles of a 30 second (s) 95° C. denaturation; 30 s 54° C. annealing; and 30 s 72° C. extension; and a final 2 min extension at 72° C.).

AS-PCR 50 uL reaction mixes will contain template DNA (2 ng), 30 pMoles of each primer flanking the target sequence, 0.2 mM of each dNTPs, 1.5 mM MgCl and 3 units of Taq Polymerase. Cycling conditions, 2 minute (min) denaturation at 95° C.; followed by 35 cycles of a 30 second (s) 95° C. denaturation; 30 s 54° C. annealing; and 30 s 72° C. extension; and a final 2 min extension at 72° C.).

First Round Primers:
muEPO-R30U21
5' CCC AAG CCC AGA GAG CGA GTT 3'    (SEQ ID NO: 9)

muEPO-R951L
5' GAA TAA GAC GAA TCA AGG 3'    (SEQ ID NO: 10)

AS-PCR Primers
muEPO-R834L21
5' GGC TTC ACC AAT CCC GTT CAA 3'    (SEQ ID NO: 11)
or muEPO-R951L
5' GAA TAA GAC GAA TCA AGG 3'    (SEQ ID NO: 12)
and As-PCR-C
5' GACCCTGTGACTATGGATT 3'    (SEQ ID NO: 13)

Using test systems, RFLP analysis was readily able to detect as few as 3 mutant events per 2,000 wild-type genomes.

---

We claim:

1. A method of detecting and isolating a cell in a culture, which cell is mutated by a sequence-specific process, the method comprising:
   a) treating the culture with a sequence-specific process that introduces a 3' and a 5' mutation in a genomic target, wherein the 3' and 5' mutations are separated by not more than 100 nucleotides;
   b) forming replicate subcultures of the treated culture;
   c) making a first polymerase chain reaction (PCR) product that contains the site of the 3' and 5' mutations using a sample of genomic DNA from a replicate of at least two subcultures of the treated culture;
   d) making a second PCR product that contains the site of the 5' mutation using the first PCR product, an allele-specific polymerase chain reaction (AS-PCR) primer that encodes the 3' mutation and a forward primer that is not homologous to the site of the 5' mutation;
   e) identifying a positive subculture by the presence of the 5' mutation in the second PCR product using template from the subculture;
   f) subdividing a replicate of the positive subculture;
   g) identifying a positive subdivision of the positive subculture by the presence of the 5' mutation in cells of the subdivision; and
   h) verifying that the positive subdivision contains a doubly substituted cell having both the 3' and 5' mutations and cloning the doubly substituted cell,
   wherein the sequence-specific process is short fragment homologous replacement (SFHR), the SFHR comprising the use of an exogenous nucleic acid having a sense strand, an antisense strand, or both.

2. The method of claim 1, wherein step (g) is performed by reiteration of steps (b) through (f) with the modification that in each subsequent iteration of step (b) the subcultures are the subdivisions formed by the previous iteration of step (f).

3. The method of claim 2, wherein step (g) is performed at least twice by reiterations of modified steps (b) through (f).

4. The method of claim 1, wherein the 3' terminal of the AS-PCR primer encodes the 3' mutation.

5. The method of claim 1, wherein the presence of the 5' mutation is identified by a restriction enzyme digest.

6. The method of claim 1, wherein the presence of the 5' mutation is identified by pyrosequencing.

7. The method of claim 1, wherein the presence of the 5' mutation is identified by a hybridization-dependent enzymatic degradation of an oligonucleotide probe that is labeled with a fluorescent dye and a quenching dye, wherein said degradation results in separation of the fluorescent and the quenching dye.

8. The method of claim 1, wherein the exogenous nucleic acid is substantially free of the antisense strand.

9. The method of claim 1, wherein the exogenous nucleic acid is substantially free of the sense strand.

10. The method of claim 1, wherein the mutated cell is a yeast cell.

11. The method of claim 1, wherein the mutated cell is a mammalian cell.

12. The method of claim 1, wherein the mutated cell is a plant cell.

13. The method of claim 4, wherein the exogenous nucleic acid is substantially free of the antisense strand.

14. The method of claim 4, wherein the exogenous nucleic acid is substantially free of the sense strand.

15. The method of claim 4, wherein the mutated cell is a yeast cell.

16. The method of claim 4, wherein the mutated cell is a mammalian cell.

17. The method of claim 4, wherein the mutated cell is a plant cell.

18. The method of claim 1, wherein making a second PCR product comprises a PCR reaction conducted at a reduced level of hybridization stringency relative to hybridization stringencies that suppress the amplification of a first PCR template lacking the 3' mutation.

19. The method of claim 18, wherein the second PCR product is produced in an amount that is not significantly affected by the presence or absence of the 3' mutation.

20. The method of claim 18, wherein the PCR reaction is conducted at an annealing temperature that results in 500-fold to 1000-fold preferential amplification of a mutated template versus a nonmutated template.

21. The method of claim 1, wherein the 3' and 5' mutations are separated by between 1 and 50 nucleotides.

22. A method of detecting and isolating a cell in a culture, the cell having a 3' and a 5' mutation in a genomic target, the method comprising:
   a) forming replicate subcultures of a culture comprising the cell;
   b) making a first polymerase chain reaction (PCR) product that contains the site of the 3' and 5' mutations using a sample of genomic DNA from a replicate of at least two subcultures of the culture;
   c) making a second PCR product that contains the site of the 5' mutation using the first PCR product, an allele-specific polymerase chain reaction (AS-PCR) primer that encodes the 3' nucleotide mutation and a forward primer that is not homologous to the site of the 5' mutation;

d) identifying a positive subculture by the presence of the 5' mutation in the second PCR product using template from the subculture;

e) subdividing a replicate of the positive subculture;

f) identifying a positive subdivision of the positive subculture by the presence of the 5' mutation in cells of the subdivision; and g) verifying that the positive subdivision contains a doubly substituted cell having both the 3' and 5' mutations and cloning the doubly substituted cell.

23. The method of claim 22, wherein the 3' and 5' mutations are separated by not more than 100 nucleotides.

24. The method of claim 23, wherein the 3' and 5' mutations are separated by between 1 and 50 nucleotides.

25. The method of claim 22, wherein making a second PCR product comprises a PCR reaction conducted at a reduced level of hybridization stringency relative to hybridization stringencies that suppress the amplification of a first PCR template lacking the 3' mutation.

26. The method of claim 25, wherein the second PCR product is produced in an amount that is not significantly affected by the presence or absence of the 3' mutation.

27. The method of claim 25, wherein the PCR reaction is conducted at an annealing temperature that results in 500-fold to 1000-fold preferential amplification of a mutated template versus a nonmutated template.

* * * * *

SEQUENCE LISTING

<160> NUMBER OF SEQ ID NOS: 13

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
tcggggtagc ggctgaagca c    21

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
catggcacaa gtcactgtgg    20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ccacctgcac acaaggtgcc    20

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
aacaggacca acactgggct g    21

<210> SEQ ID NO 5
<211> LENGTH: 18
<212> TYPE: DNA
<213> ORGANISM: Artificial Sequence
<220> FEATURE:
<223> OTHER INFORMATION: primer -continued

```
<400> SEQUENCE: 5
ggctgcctgg agacatcc                                                   18

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
gcccactcca atgggcacg                                                  19

<210> SEQ ID NO 7
<211> LENGTH: 21
<212> TYPE: DNA
<213> ORGANISM: Homo sapiens

<400> SEQUENCE: 7
ggagacatcc aggtcgtgcc c                                               21

<210> SEQ ID NO 8
<211> LENGTH: 21
<212> TYPE: DNA
<213> ORGANISM: Homo sapiens

<400> SEQUENCE: 8
ggagacatct aggtggtgcc c                                               21

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
cccaagccca gagagcgagt t                                               21

<210> SEQ ID NO 10
<211> LENGTH: 18
<212> TYPE: DNA
<213> ORGANISM: Artificial Sequence
<220> FEATURE:
<223> OTHER INFORMATION: primer

<400> SEQUENCE: 10
gaataagacg aatcaagg                                                   18

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
ggcttcacca atcccgttca a                                               21

<210> SEQ ID NO 12
<211> LENGTH: 18
<212> TYPE: DNA
<213> ORGANISM: Artificial Sequence
<220> FEATURE:
<223> OTHER INFORMATION: primer
```

```
-continued

<400> SEQUENCE: 12
gaataagacg aatcaagg                                                         18

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
gaccctgtga ctatggatt                                                        19
```